United States Patent [19]

Lange et al.

[11] 4,268,695

[45] May 19, 1981

[54] PROCESS FOR THE CONTINUOUS PREPARATION OF BUTANE-1,4-DIOL

[75] Inventors: Erhard Lange; Manfred Z. Hausen, both of Marl, Fed. Rep. of Germany

[73] Assignee: Chemische Werke Huls Aktiengesellschaft, Marl, Fed. Rep. of Germany

[21] Appl. No.: 84,279

[22] Filed: Oct. 12, 1979

[30] Foreign Application Priority Data

Oct. 21, 1978 [DE] Fed. Rep. of Germany ....... 2845905

[51] Int. Cl.³ ............................................. C07C 31/20
[52] U.S. Cl. .................................................... 568/864
[58] Field of Search ........................................ 568/864

[56] References Cited

U.S. PATENT DOCUMENTS

| | | | |
|---|---|---|---|
| 2,094,611 | 10/1937 | Lazier | 568/864 |
| 3,478,112 | 11/1969 | Adam et al. | 568/864 |
| 3,772,395 | 11/1973 | Yamaguchi et al. | 568/864 |
| 3,830,830 | 8/1974 | Cleveland et al. | 568/864 |
| 4,032,458 | 6/1977 | Cooley et al. | 568/864 |
| 4,155,919 | 5/1979 | Ramioulle et al. | 568/864 |

FOREIGN PATENT DOCUMENTS 1454440 11/1976 United Kingdom .
1464263 2/1977 United Kingdom .

OTHER PUBLICATIONS

Zymalkowski, "Katalytische Hydrierungen", Stuttgart (1965), p. 116.

*Primary Examiner*—Joseph E. Evans
*Attorney, Agent, or Firm*—Millen & White

[57] ABSTRACT

A continuous process for the preparation of butane-1,4-diol comprises, in a one-stage process, catalytically hydrogenating a solution of maleic anhydride in a monohydric aliphatic alcohol, in the presence of hydrogen and a copper chromite catalyst.

10 Claims, No Drawings

PROCESS FOR THE CONTINUOUS PREPARATION OF BUTANE-1,4-DIOL

BACKGROUND OF THE INVENTION

Butane-1,4-diol can be prepared by direct hydrogenation of maleic anhydride.

According to U.S. Pat. Nos. 2,772,291 and 2,772,292, such a process is carried out at high pressures of up to 700 bar, using nickel molybdate or nickel chromate as the catalyst. The yields of butane-1,4-diol are at most 53%. Substantial amounts of tetrahydrofuran and butyrolactone are formed as by-products.

Using Raney cobalt in a discontinuous process, the process of U.S. Pat. No. 2,772,293, yields about 64% of butane-1,4,-diol, and Raney nickel only yields at most 12%. Moreover, Raney nickel and Raney cobalt are unsuitable for industrial use since they become inactivated by the acids formed from the maleic anhydride.

All these processes are operated at high pressures of 700 to 800 bar, which industrially can only be achieved at great expense, especially in view of the low yields of butane-1,4-diol.

German Auslegeschrift No. 2,133,768 (equivalent to British Pat. No. 1,320,839) proposes cobalt-rhenium and cobalt-rhenium-molybdenum compounds as catalysts stable to acids. However, the reaction product contains only 4 to 14 mole percent of the desired butane-1,4-diol.

A single-stage process using maleic anhydride as the starting material is described in German Offenlegungsschrift No. 2,519,817. It uses catalysts containing elements or compounds of elements of sub-groups VII and VIII of the periodic table, which however are not a subject of the present invention.

In German Offenlegungsschrift No. 2,543,673 (equivalent to British Pat. No. 1,454,440) maleic anhydride is reacted, in a first stage, with lower monohydric aliphatic alcohols in the absence of an esterification catalyst to give the maleic acid dialkyl ester. After the ester is isolated, it is hydrogenated, in a second stage, in the presence of a copper chromite catalyst, to give butanediol. According to German Offenlegungsschrift No. 2,553,959 (equivalent to British Pat. No. 1,464,263), esterification catalysts are additionally used in the first stage of the process described above. For the operation of these two processes it is necessary to isolate the maleic acid dialkyl ester free from acid and water under precise conditions, in order to avoid a loss of activity of the catalyst in the hydrogenation stage. It is expressly stated that copper chromite catalysts can rapidly become inactivated if free acids or acid-containing esters are fed to the hydrogenation stage. The monograph by Zymalkowski "Katalytische Hydrierungen" ("Catalytic Hydrogenations"), Stuttgart (1965), page 116, confirms these disadvantages.

SUMMARY OF THE INVENTION

Accordingly, it is an object of this invention to provide a process by means of which butane-1,4-diol is obtained in high yields from maleic anhydride in a single-stage hydrogenation process without inactivation of the catalyst and which is readily adapted to easy industrial operability.

Upon further study of the specification and appended claims, further objects and advantages of this invention will become apparent to those skilled in the art.

These objects have been attained by providing a continuous process for the preparation of butane-1,4-diol comprising, in a one-stage process, catalytically hydrogenating a solution of maleic anhydride in a monohydric aliphatic alcohol, in the presence of hydrogen and a copper chromite catalyst.

DETAILED DESCRIPTION

It has been found, surprisingly, that maleic anhydride can be hydrogenated to butane-1,4-diol in one stage over a copper chromite catalyst without inactivation of the catalyst if maleic anhydride dissolved in a monohydric aliphatic alcohol is used. Maleic anhydride is in general readily soluble in such alcohols, with partial formation of half-esters. Advantageously, the solutions are prepared at room temperature or moderately elevated temperature, for example at 15°-60° C. In general, the molar ratio of anhydride to alcohol is 1:1–1:50. It is advantageous if the alcohol is used in stoichiometric amounts, i.e., 2 moles of alcohol per mole of maleic anhydride. Better conversions of the maleic anhydride are achieved if the alcohol is used in stoichiometric excess, e.g., up to molar ratios of maleic anhydride:alcohol of 1:20, preferably 1:2–1:15. The use of a 5–50, preferably 20 percent strength by weight solution of maleic anhydride in an aliphatic alcohol is particularly appropriate. This corresponds, in the case of butanol, to a molar ratio of maleic anhydride:butanol of 1:5.3.

All monohydric aliphatic alcohols are suitable as long as the anhydride is sufficiently soluble therein and it is otherwise system compatible. Preferred suitable monohydric aliphatic alcohols include $C_1$-$C_6$ branched or straight-chain alcohols, such as, for example, methanol, n- and iso-propanol, n- and iso-butanol, hexanols, etc. or mixtures thereof. In particular, $C_4$-alcohols, such as n- or iso-butanol, can be employed for the process of this invention, because, with these alcohols, the best yields of butane-1,4-diol are achieved. Furthermore, the water of reaction formed upon hydrogenation of the maleic anhydride can be easily separated from the alcohol by azeotropic distillation when the material discharged from the hydrogenation reaction is worked up. Methanol does not form an azeotrope with water, while $C_6$-alcohols require a higher energy of vaporization.

The maleic anhydride can be dissolved in the alcohol continuously or discontinuously, in a conventional acid-resistant apparatus. As is known, partial esterification of the maleic anhydride occurs upon dissolution. The heat of reaction generated on formation of these half-esters is, in the case of iso-butanol, about 33 kJ/mol and can, if necessary, be easily removed. Complete formation of the half-ester is not necessary for any of the solvents; however, the maleic anhydride should be completely dissolved, to prevent blockages of metering pumps or of the catalyst.

The alcoholic maleic anhydride solution, hereinafter also referred to as the solution mixture, is fed continuously together with hydrogen, and without further treatment or working-up, over a copper chromite catalyst. Suitable catalysts include pure copper chromite. However, catalysts which contain an excess of copper oxide and/or contain a stabilizer, such as barium oxide, are preferred. Commercial tablet-shaped copper chromite catalysts contain, for example, about 33 percent by weight of CuO, about 38 percent by weight of $Cr_2O_3$ and about 8 percent by weight of BaO; or, for example, 37 percent by weight of CuO and 52 percent by weight of $Cr_2O_3$. Furthermore, minor amounts of silicon dioxide, aluminum oxide, alkali metal oxides or alkaline earth metal oxides may also be present. The specific surface area of such catalysts is 10–50 m²/g and the pore volume is 0.4–0.8 cm³/g. Before use, these catalysts can be washed with virtually ion-free water, such as, for example, condensed steam, in order to remove all water-soluble constituents. It is highly preferred that such water-soluble constituents be removed. It is advantageous to dry such washed catalysts, e.g., in a hydrogenation apparatus and reduce them at 180°–260° C., and 250–350 bar pressure, advantageously at 200° C. and 300 bar pressure, in a stream of hydrogen, before they are subjected to the reaction mixture.

The hydrogen can be introduced into the hydrogenation apparatus together with the solution mixture, co-currently or counter-currently. Hydrogenation can also be carried out by bubbling hydrogen through the solution mixture phase. Preferably, hydrogen and the solution mixture are passed downwardly in co-current flow over the catalyst fixedly located in a hydrogenation furnace.

In order to be able, where necessary, to remove the heat of hydrogenation more effectively and to achieve a uniform temperature profile over the entire catalyst bed, the hydrogen and also a part of the material discharged from the hydrogenation reaction can be recycled to the hydrogenation furnace.

The quality of the results of the hydrogenation reaction is, inter alia, dependent on the throughput of the solution mixture over the catalyst. The throughput for the successful performance of the reaction can vary within wide limits; but a throughput of about 0.1–0.5, especially 0.2 liter of solution mixture per liter of catalyst and per hour has proved advantageous, with the solution mixture containing about 5 to 50, especially 20, percent by weight of maleic anhydride.

The hydrogenation can be carried out at pressures of 250 to 350 bar, preferably at 290 to 310 bar, and especially at about 300 bar hydrogen pressure. Suitable reaction temperatures are 180° to 300° C. and are preferably 200°–260° C.

Slight losses in activity of the catalyst during the reaction period can be compensated by slowly raising the temperature. The activity of the catalyst remains constant over a long period of time in spite of the exposure to carboxylic acids formed as intermediates and to the water of reaction. The reaction conditions of this invention virtually preclude attack of the catalysts.

Hydrogenation furnaces of conventional construction can be used for carrying out the process of this invention, provided that they are designed for the requisite temperatures and pressures and are made of acid-resistant material.

The reaction products are advantageously separated by fractional distillation. Thereby, the solvent is recovered unchanged and can be reused to dissolve maleic anhydride. Similarly, the n-butanol formed as a by-product can be recycled as the solvent. Tetrahydrofuran, formed in small amounts, is recovered as first runnings and can be fed to some appropriate use. Other by-products formed in small amounts, such as, for example, succinic acid dialkyl esters and butyrolactone, are advantageously returned to the hydrogenation stage. Small proportions of acid in the product can be removed by treatment with alkali before the distillation.

Using the process of this invention, maleic anhydride is converted virtually quantitatively in a simple reaction. The yields of butane-1,4-diol achieved are greater than 90 mole percent, e.g., 91–98 mole percent. The formation of non-utilizable by-products is slight. Butane-1,4-diol which is more than 99.5 percent pure can be prepared by fractional distillation.

Although the preceding description is given in terms of a continuous process, if desired, the process of this invention may be carried out in batch mode employing conditions corresponding to those specified above.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

The yields mentioned in the examples refer to results obtained by gas-chromatographic analyses.

EXAMPLE 1

430 ml, corresponding to 635 g, of copper chromite catalyst are introduced into a vertical electrically heated hydrogenation furnace of stainless steel (for example 16,5–18,5 percent by weight Cr, 10,5–12,5 percent by weight Ni, 2,0–2,5 percent by weight Mo, rest Fe), having an internal diameter of 24 mm and a length of 1,200 mm.

The catalyst employed contains, in the non-reduced state, about 37 percent by weight of CuO, about 52 percent by weight of $Cr_2O_3$ and about 8 percent by weight of $SiO_2$. After washing out soluble constituents with steam condensate, the catalyst is reduced at 200° C. in a stream of hydrogen at 300 bar. The reduction has ended after about 2 hours. Maleic anhydride is dissolved in iso-butanol in the weight ratio of 1:4 corresponding to a molar ratio of 1:5.3, by stirring at a temperature of 25° C. The solution mixture and hydrogen are introduced together at the top of the hydrogenation furnace. The throughput is 0.17 ml of solution mixture/ml of catalyst per hour. Hydrogen is introduced directly and the amount of off-gas is set to 400 Nl of hydrogen/hour. The hydrogenation is carried out at a pressure of 300 bar.

The reaction temperature is initially 210° C. Over the duration of the experiment, it is raised to 230° C. The reaction mixture leaving the furance is cooled, run from a product stripper into a receiver and separated into two fractions by distillation. The first fraction consists of alcohol recovered unchanged, small amounts of tetrahydrofuran and n-butanol, and the water formed during the reaction. The residue in the main fraction contains the desired butane-1,4-diol, small proportions of butyrolactone, traces of succinic acid diisobutyl ester and small amounts of higher-boiling constituents. The acid number of the residue is 0.2. Conversion of the maleic anhydride is virtually complete and the yield of butane-1,4-diol is 92.8 mole percent; an additional 4.0 mole percent of the maleic anhydride has been converted to tetrahydrofuran, 0.8 mole percent to butyrolactone, 0.1 mole percent to succinic acid diisobutyl ester and 2.3 mole percent to other compounds. After 82 days of operation, the catalyst shows no loss of its activity.

EXAMPLE 2 n-Butanol is used as the solvent for the maleic anhydride. The weight ratio of maleic anhydride:n-butanol is 1:4. The method of carrying out the experiment and the composition of the catalyst correspond to Example 1. The amount of catalyst is 400 ml and the throughput is 0.18 ml of solution/ml of catalyst per hour. The reaction temperature is between 210° and 220° C. and the hydrogen pressure is 290 bar. The amount of off-gas is set at 200 ml of hydrogen/hour. After separating the reaction mixture, which has an acid number of 0.1, by distillation, the following yields are found, conversion of the maleic anhydride being virtually complete: 93.6 mole percent of butane-1,4-diol, 1.6 mole percent of butyrolactone, 3.2 mole percent of tetrahydrofuran, traces of succinic acid di-n-butyl ester and 1.6 mole percent of other by-products. After 23 days of operation, the catalyst activity remains as good as before.

EXAMPLE 3

In an experimental reactor, as described in Example 1, a solution of 20 parts of maleic anhydride in 80 parts of iso-butanol is hydrogenated over a BaO-stabilized copper chromite catalyst which in the non-reduced and non-washed state contains about 33 percent by weight of CuO, about 38 percent by weight of $Cr_2O_3$, about 8 percent by weight of BaO, about 8% by weight of $SiO_2$ and 3% of $Na_2O$. The throughput is 0.2 ml of solution/ml of catalyst per hour, at a temperature of between 210° and 220° C. and a hydrogen pressure of 300 bar. The amount of hydrogen employed is set at 400 liters/hour. The material discharged from the hydrogenation reaction has an acid number <0.1. Gas-chromatographic examination of the reaction product, which has been separated by distillation, shows a yield of 91.0 mole percent of butane-1,4-diol. The maleic anhydride has been converted virtually completely. In addition, 3.5 mole percent of tetrahydrofuran and 2.0 mole percent of other by-products have formed. 0.6 mole percent of butyrolactone and 2.9 mole percent of succinic acid diisobutyl ester can be recycled into the hydrogenation stage.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A continuous process for the preparation of butane-1,4-diol consisting essentially of, in a one-stage process, catalytically hydrogenating the solution which results when maleic anhydride is dissolved in a monohydric aliphatic alcohol, the hydrogenation being carried out in the presence of hydrogen and a copper chromite catalysts at a pressure of 250-350 bar and a temperature of 180°-300° C., thereby preparing butane-1,4-diol.

2. The process of claim 1 wherein the hydrogen and the maleic anhydride dissolved in the monohydric aliphatic alcohol are co-currently downwardly flowed over the catalyst fixedly located in a hydrogenation furnace.

3. The process of claim 1 wherein the monohydric aliphatic alcohol has 1–6 carbon atoms.

4. The process of claim 3 wherein the alcohol is a $C_4$-monohydric aliphatic alcohol.

5. The process of claim 1 wherein the maleic anhydride is provided to the hydrogenation reaction in a monohydric aliphatic alcohol solution having the molar ratio of maleic anhydride:alcohol of 1:2–1:20, at room temperature.

6. The process of claim 1 wherein the maleic anhydride is employed as a 20 percent strength solution in monohydric aliphatic alcohol.

7. The process of claim 2 wherein the hydrogenation is carried out at a reaction temperature of 200°–260° C. and a reaction pressure of 290–310 bar.

8. The process of claim 1 wherein the catalyst is pure copper chromite; or copper chromite containing an excess of copper oxide, a stabilizer or both an excess of copper oxide and a stabilizer.

9. The process of claim 8 wherein the stabilizer is barium oxide.

10. The process of claim 1 wherein, prior to hydrogenation, the catalyst is washed with water to remove water soluble material, dried and reduced with hydrogen.

* * * * *